United States Patent [19]

Lavanish

[11] 4,252,960
[45] Feb. 24, 1981

[54] INTERMEDIATES OF AND METHODS OF MAKING 3-[5-[1-(NITROPHENOXY)ALKYL, ALKYNYL, ALKENYL OR HALOALKYL]-1,3,4-THIADIAZOL-2-YL]-4-HYDROXY-1-METHYL-2-IMIDAZOLIDI-NONES

[75] Inventor: Jerome M. Lavanish, Akron, Ohio

[73] Assignee: PPG Industries, Inc., Pittsburgh, Pa.

[21] Appl. No.: 123,333

[22] Filed: Feb. 21, 1980

Related U.S. Application Data

[62] Division of Ser. No. 49,018, Jun. 18, 1979.

[51] Int. Cl.$^3$ ............................................. C07D 285/12
[52] U.S. Cl. ........................................ 548/138; 71/90; 548/136; 548/140
[58] Field of Search ........................................... 548/138

[56] References Cited

U.S. PATENT DOCUMENTS

| | | |
|---|---|---|
| 3,758,492 | 9/1973 | Metzger et al. ...................... 548/137 |
| 3,759,939 | 9/1973 | Metzger et al. ...................... 548/137 |
| 3,849,432 | 11/1974 | Metzger et al. ...................... 548/137 |
| 3,901,904 | 8/1975 | Krenzer ...................... 548/137 |
| 3,901,905 | 8/1975 | Krenzer ...................... 548/137 |
| 3,904,640 | 9/1975 | Krenzer ...................... 548/137 |
| 3,920,674 | 11/1975 | Krenzer ...................... 548/137 |
| 3,925,402 | 12/1975 | Krenzer ...................... 548/137 |
| 3,964,895 | 6/1976 | Krenzer ...................... 548/137 |
| 4,012,223 | 3/1977 | Krenzer ...................... 548/137 |
| 4,023,957 | 5/1977 | Krenzer ...................... 548/137 |
| 4,028,375 | 6/1977 | Krenzer ...................... 548/137 |
| 4,036,848 | 7/1977 | Krenzer ...................... 548/137 |
| 4,052,191 | 10/1977 | Krenzer ...................... 548/137 |
| 4,093,443 | 6/1978 | Krenzer ...................... 548/137 |

*Primary Examiner*—Alton D. Rollins
*Attorney, Agent, or Firm*—Edward J. Whitfield; Robert J. Grassi

[57] ABSTRACT

The disclosed compounds such as 3-[5-[1-(2-nitrophenoxy)ethyl]-1,3,4-thiadiazol-2-yl]-4-hydroxy-1-methyl-2-imidazolidinone are useful for preemergence control of weeds such as jimsonweed.

2 Claims, No Drawings

INTERMEDIATES OF AND METHODS OF MAKING 3-[5-[1-(NITROPHENOXY)ALKYL, ALKYNYL, ALKENYL OR HALOALKYL]-1,3,4-THIADIAZOL-2-YL]-4-HYDROXY-1-METHYL-2-IMIDAZOLIDINONES

This is a division of application Ser. No. 49,018, filed June 18, 1979.

BACKGROUND OF THE INVENTION

1. Field of the Invention

The invention relates to substituted 1,3,4-thiadiazol-2-yl-4-hydroxy-1-methyl-2-imidazolidinone, particularly to the 3-[5-[1-(nitrophenoxy), -alkyl, -alkynyl, -alkenyl, or haloalkyl]-1,3,4-thiadiazol-2-yl]-4-hydroxy-1-methyl-2-imidazolidinone compounds.

2. Description of the Prior Art

The prior art describes imidazolidinones, but the prior art is silent concerning the novel herbicidal compounds described herein and their use to control the weeds described herein.

SUMMARY OF THE INVENTION

The invention described herein concerns compounds graphically represented by Formula I.

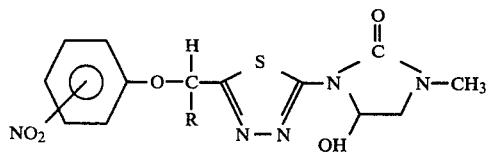

wherein:

R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 2-bromoethyl; the intermediates graphically represented by Formulas III, IV and V,

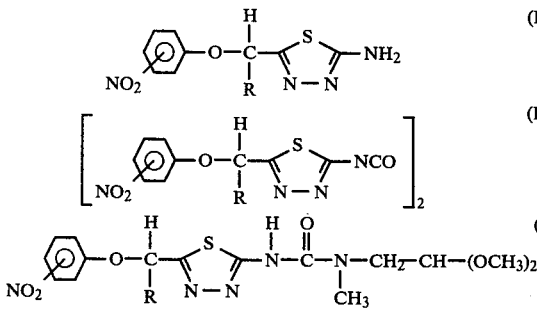

wherein:

R is defined as herein, as well as the process for making compounds of the described formulas. The compounds of Formula I are particularly useful for controlling weeds preemergence and are selective to other weeds preemergence at low rates of application. Particularly, the compounds wherein R is methyl or ethyl. For example, the compound where R is methyl, and the nitro (—NO₂) is at the ortho (2-position) on the phenoxy part of the compound, is useful for controlling wild mustard, morningglory, and crabgrass, johnsonweed and coffeeweed at preemergence rates of five pounds per acre.

DESCRIPTION OF THE PREFERRED EMBODIMENT

The novel agriculturally useful compounds described herein may be graphically represented by Formula I:

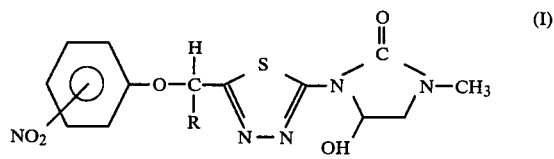

wherein:

R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 3-bromoethyl.

Examples of compounds represented by Formula I are:

3-[5-(1-(2-nitrophenoxyethyl)-1,3,4-thiadiazol-2-yl]-4-hydroxy-1-methyl-2-imidazolidinone.

3-[5-(1-(3-nitrophenoxy)-2-bromoethyl)-1,3,4-thiadiazol-2-yl]-4-hydroxy-1-methyl-2-imidazolidinone.

3-[5-(1-(4-nitrophenoxy)-2-bromoethyl)-1,3,4-thiadiazol-2-yl]-4-hydroxy-1-methyl-2-imidazolidinone.

3-[5-(1-(2-nitrophenoxy)-3-chloropropyl)-1,3,4-thiadiazol-2-yl]-4-hydroxy-1-methyl-2-imidazolidinone.

3-[5-(1-(3-nitrophenoxy)-3-bromopropyl)-1,3,4-thiadiasol-2-yl]-4-hydroxy-1-methyl-2-imidazolidinone.

3-[5-(1-(4-nitrophenoxy)-2-propynyl)-1,3,4-thiadiazol-2-yl]-4-hydroxy-1-methyl-2-imidazolidinone.

3-[5-(1-(2-nitrophenoxy)-2-butenyl)-1,3,4-thiadiazol-2-yl]-4-hydroxy-2-methyl-2-imidazolidinone.

3-[5-(1-(3-nitrophenoxy)-3-butenyl)-1,3,4-thiadiazol-2-yl]-4-hydroxy-1-methyl-2-imidazolidinone.

3-[5-(1-(4-nitrophenoxy)-2-propenyl)-1-3-4-thiadiazol-2-yl]-4-hydroxy-1-methyl-2-imidazolidinone.

3-[5-(1-(2-nitrophenoxy)-1-butenyl)-1,3,4-thiadiazol-2-yl]-4-hydroxy-1-methyl-2-imidazolidinone.

3-[5-(1-(3-nitrophenoxy)-2-chloroethyl)-1,3,4-thiadiazol-2-yl]-4-hydroxy-1-methyl-2-imidazolidinone.

3-[5-(1-(4-nitrophenoxy)-2-bromoethyl)-1,3,4-thiadiazol-2-yl]-4-hydroxy-1-methyl-2-imidazolidinone.

3-[5-(1-(2-nitrophenoxy)-3-chloropropyl)-1,3,4-thiadiazol-2-yl]-4-hydroxy-1-methyl-2-imidazolidinone.

3-[5-(1-(3-nitrophenoxy)-3-bromopropyl)-1,3,4-thiadiazol-2-yl]-4-hydroxy-1-methyl-2-imidazolidinone.

3-[5-(1-(4-nitrophenoxy)-3-butenyl)-1,3,4-thiadiazol-2-yl]-4-hydroxy-1-methyl-2-imidazolidinone.

3-[5-(1-(2-nitrophenoxy)-2-pentenyl)-1,3,4-thiadiazol-2-yl]-4-hydroxy-1-methyl-2-imidazolidinone.

3-[5-(1-(3-nitrophenoxy)-(3-methylbutyl)-1,3,4,-thiadiazol-2-yl]-4-hydroxy-1-methyl-2-imidazolidinone.

3-[5-(1-(4-nitrophenoxy)-(2-methylbutyl)-1,3,4-thiadiazol-2-yl]-4-hydroxy-1-methyl-2-imidazolidinone.

3-[5-(1-(2-nitrophenoxy)-2,2-dimethylpropyl)-1,3,4-thiadiazol-2-yl]-4-hydroxy-1-methyl-2-imidazolidinone.

3-[5-(1-(3-nitrophenoxy)butyl)-1,3,4-thiadiazol-2-yl]-4-hydroxy-1-methyl-2-imidazolidinone.

3-[5-(1-(4-nitrophenoxy)-2-methylpropyl)-1,3,4-thiadiazol-2-yl]-4-hydroxy-1-methyl-2-imidazolidinone.

3-[5-(1-(2-nitrophenoxy)propyl)-1,3,4-thiadiazol-2-yl]-4-hydroxy-1-methyl-2-imidazolidinone.

Although all of the compounds described herein are useful for the purpose described herein, some compounds are more useful than others. Compounds in which R is an alkynyl are of a general utility, however, compounds in which R is an alkenyl are of better utility. Compounds in which R is a haloalkyl described herein are of high utility and of these, the preferred compounds are those in which R is chloromethyl or bromomethyl. Compounds in which R is an alkyl described herein, are highly preferred and especially preferred are compounds in which the alkyl is methyl or ethyl.

The following compounds are the most preferred:

3-[5-(1-(2-nitrophenoxy)propyl)-1,3,4-thiadiazol-2-yl]-4-hydroxy-1-methyl-2-imidazolidinone.

3-[5-(1-(2-nitrophenoxy)ethyl)-1,3,4-thiadiazol-2yl]-4-hydroxy-1-methyl-2-imidazolidinone.

3-[5-(1-(3-nitrophenoxy)propyl)-1,3,4-thiadiazol-2-yl]-4-hydroxy-1-methyl-2-imidazolidinone.

3-[5-(1-(3-nitrophenoxy)ethyl)-1,3,4-thiadiazol-2-yl]-4-hydroxy-1-methyl-2-imidazolidinone.

3-[5-(1-(4-nitrophenoxy)propyl)-1,3,4-thiadiazol-2-yl]-4-hydroxy-1-methyl-2-imidazolidinone.

3-[5-(1-(4-nitrophenoxy)propyl)-1,3,4-thiadiazol-2-yl]-4-hydroxy-1-methyl-2-imidazolidinone.

[5-(1-(4-nitrophenoxy)ethyl)-1,3,4-thiadiazol-2-yl]-4-hydroxy-1-methyl-2-imidazolidinone.

SYNTHESIS OF THE COMPOUNDS

The synthesis of the compound proceeds according to the general reactions of 1, 2, 3 and 4 shown below:

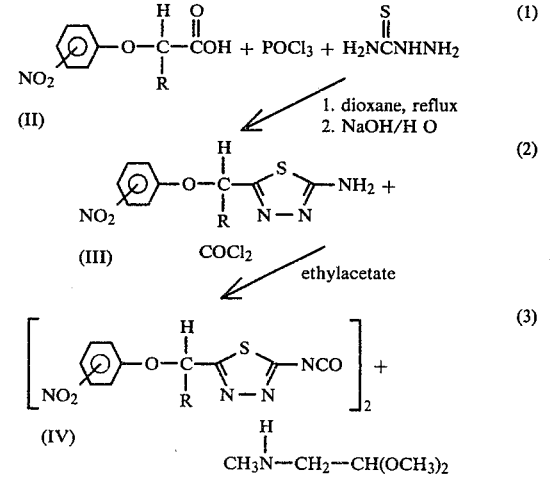

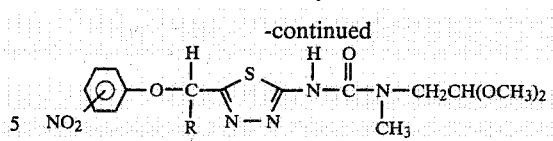

PREPARATION OF 5-SUBSTITUTED 2-AMINO-1,3,4-THIADIAZOL

The proper alpha substituted carboxylic acid graphically represented by Formula II, wherein R is as described herein (typically 0.4–0.5 moles), an equimolar amount of thiosemicarbazide, and 30 milliliters of dry dioxane, are charged into a hundred milliliter reactor equipped with a thermometer, an efficient stirrer, pressure equilizer, addition funnel, and a condenser-drying tube. The additional funnel is charged with approximately 10 percent excess of phosphorous oxychloride which is added drop-wise to as to maintain a reaction temperature of 85°–95° C. and reaction occurs as shown by reaction equation 1. The mixture is then heated to reflux for about 1 hour, after which the solvent is flashed off using a vacuum such as a water aspirator. Water (50 milliliters) is added to the residue to give an emulsion which is then made basic with a 50% sodium hydroxide solution. In those instances that a solid product is obtained (graphically represented by Formula III, wherein R is as described herein) the product is isolated by filtration, and recrystallized when necessary. In other cases, the reaction mixture is extracted with ether, the ether layer is separated from the heavier layers, dried over magnesium sulfate, filtered and concentrated under vacuum to give the crude product represented as a viscous oil.

PREPARATION OF THE ISOCYANATE DIMERS

Five to 10 grams of the appropriate 2-amino-1,3,4-thiadiazole (graphically represented by Formula III) is added to a solution of phosgene in ethylacetate, (or other suitable solvent) prepared by saturating 50–100 milliliters of solvent with phosgene at room temperature then adding another 50–100 milliliters of solvent. The mixture is allowed to stir overnight at room temperature to react as shown by reaction equation 2, and then purged with nitrogen or argon to remove the unreacted phosgene. In those cases where a solid was obtained, the product (graphically represented by Formula IV) which is an isocyanate dimer of the appropriate substituted 1,3,4-thiadiazol) was isolated by filtration and dried. In cases where no solid product is evident, the reaction mixture may be topped under vacuum to give the product as a viscous oil or glass.

PREPARATION OF ACETAL UREAS

The appropriate isocyanate dimer of Formula IV and an equivalent amount of methylaminoacidaldehyde dimethylacetal were heated to reflux (5–15 minutes) in an inert solvent such as ether, benzene or toluene, and the reaction proceeded as shown by reaction equation 3 so as to form the product graphically represented by Formula V. Some products may be produced as crystals directly from solution, but others may be induced by addition of hexane. The product represented by Formula V may be purified such as by washing with ether, or hexane or recrystallized from hexane/benzene or from ether/benzene, or from ether/chloroform/benzene solutions. Those products that are represented by Formula V obtained as oils need not be purified.

PREPARATION OF THE COMPOUNDS OF FORMULA I

The appropriate acetal urea of Formula V (approximately three to four grams) is added to 150–200 milliliters of water containing 1.5–2 milliliters of concentrated hydrochloric acid. The mixture is stirred vigorously and heated to reflux, and reaction proceeds as shown by reaction equation 4. The hydrolysis is monitored by thin layer chromatography (alumna-ethylacetate) until complete, and the product containing a compound of Formula I forms. The product, in some cases, may be crystallized directly from the reaction mixture upon cooling. In other cases, the compounds of Formula I are extracted with chloroform and isolated by stripping the solvent under vacuum. Those compounds which solidify upon concentration are further purified. In some cases, the compounds may be used directly as obtained. In other cases, crystallization is induced by seeding an ether solution with a related compound, which may then be further purified.

EXAMPLES

The following examples illustrate the synthesis of the compounds described herein.

Example I

SYNTHESIS OF 3-[5-(1-(2-nitrophenoxy) ethyl)-1,3,4-thiadiazol-2-yl]-4-hydroxy-1-methyl-2-imidazolidinone a. Formation of 5-[1-(2-nitrophenoxy) ethyl]-2-amino-1,3,4-thiadiazole A 100 milliliter, 3-neck flask adapted with a Claisen adaptor, paddle stirrer, thermometer, an addition funnel and condenser, was charged with 8.4 grams (0.040 moles) of 2-(2-nitrophenoxy)propanoic acid, (3.6 grams, 0.040 mole) of thiosemicarbazide and 30 ml. of dioxane. The slurry was heated to 90° centigrade and the addition funnel was charged with phosphorous oxychloride ($POCl_3$). The $POCl_3$ (6.7 grams, 0.044 mole) was slowly added (for 26 minutes) while maintaining the temperature within 90°–95° C., and then stirred for an additional 20 minutes. It was refluxed for 60 minutes and cooled. The flask was evacuated by using a water aspirator to remove volatiles (HCl, $POCl_3$ and some dioxane), leaving a viscous gummy residue to which 50 ml. of water was added and the slurry was made basic by adding 50 percent solution of NaOH until the pH of the solution was 10, and a solid precipate formed. The solid precipate was filtered off, washed with water, dried in a vacuum oven at 80 degrees Centigrade to tan crystals, 5-(1-(2-nitrophenoxy) ethyl)-2-amino-1,3,4-thiadiazole. (Melting point 137–142 degrees Centigrade).

b. Formation of 5-(1-(2-nitrophenoxy) ethyl)-1,3,4-thiadiazol-2-yl isocyanate dimer A 300 ml., 3-neck flask equipped with a magnetic stirrer, thermometer, dry ice condensor/drying tube and inlet from a phosgene ($COCl_2$) tank via a calibrated rotometer was charged with 50 ml. of ethylacetate which was saturated with phosgene at 20° C. An additional 50 ml. of ethylacetate was added and then 5.2 grams of 5-(1-(2-nitrophenoxy) ethyl)-2-amino-1,3,4-thiadiazole, (prepared above) was added at a temperature of about 0° C. The resulting yellow slurry was stirred overnight, and purged with nitrogen overnight. The solution was filtered through a Whatman #42 filter paper to yield a pale yellow solution which was topped with a roto-vac at 70 degrees Centigrade to form 5.2 grams of a viscous yellow oil of 5-(1-(2-nitrophenoxy) ethyl)-1,3,4-thiadiazol-2-yl isocyanate dimer.

c. Formation of 3-[5-(1-(2-nitrophenoxy) ethyl)-1,3,4-thiadiazol-2-yl]-1-methyl-1-(2,2-dimethoxyethyl) urea 2.1 grams (0.018 mole) of methylaminoacetaldehyde dimethylacetal was added to a 50 ml. benzene solution containing 5.2 grams (0.018 mole) of the 5-(1-(2-nitrophenoxy) ethyl)-1,3,4-thiadiazol-2-yl isocyanate dimer (prepared above) and the resulting solution was refluxed for 15 minutes to form a yellow solution. Hexane (100 ml.) was added and the resulting oil was allowed to stand for 72 hours and topped with a roto-vac at 70 degrees Centigrade to yield 7.2 grams of a red-orange oil of 3-[5-(1-(2-nitrophenoxy ethyl)-1,3,4-thiadiazol-2-yl]-1-methyl-1-(2,2-dimethoxyethyl)urea.

d. Synthesis of 3-[5-(1-(2-nitrophenoxy) ethyl)-1,3,4-thiadiazol-2-yl]-1-methyl-4-hydroxy-2-imidazolidinone A solution containing 7.2 grams of the 3-[5-(1-(2-nitrophenoxy ethyl)-1,3,4-thiadiazol-2-yl]-1-methyl-(2,2-dimethoxyethyl)urea (prepared above) 200 ml. of water and 2 ml. of concentrated hydrochloric acid HCl) was refluxed for 20 minutes, cooled, and the gooey solid which formed was extracted off with chloroform. The chloroform extract was dried over magnesium sulfate ($Na_2SO_4$), filtered, and topped in a roto-vac at 70 degrees Centigrade to yield 5.1 grams of a viscous yellow oil.

After standing overnight, the yellow oil was mixed with the minimum amount of diethylether, chloroform, and benzene, chromatographed on alumina by eluting with an equal volume mixture of ethylacetate and methanol. The high retention impurities were removed and the portions were collected and topped in a roto-vac at 70 degrees Centigrade to yield 3.2 grams of a yellow oil which cooled to glassy solid of 3-[5-(1-(2-nitrophenoxy) ethyl)-1,3,4-thiadiazol-2-yl]-1-methyl-4-hydroxy-2-imidazolidinone. Its IR spectra (neat) had a broad OH band at $3340^{-1}$ cm and C=O band at 1718 $cm^{-1}$.

Example II

SYNTHESIS OF 3-[5-[1-(3-nitrophenoxy)ethyl]-1,3-4-thiadiazol-2-yl]-4-hydroxy-1-methyl-2-imidazolidinone a. Formation of 5-(-1-(3-nitrophenoxy)ethyl)-2-amino-1,3,4-thiadiazole

The procedure of Example I a. was followed, to form 8.2 grams of pale yellow crystals of 5-(1-(3-nitrophenoxy)ethyl)-2-amino-1,3,4-thiadiazole (m. p. 149°–159° C.).

b. Formation of 5-(1-(3-nitrophenoxy)ethyl)-1,3,4-thiadiazol-2-yl isocyanate dimer The procedure of Example I b. was followed using 8.2 grams of the 5-(2-(3-nitrophenoxy)ethyl)-2-amino-1,3,4-thiadiazol (prepared above). After purging the mixture overnight with nitrogen, a white slurry formed, which was suction filtered, washed with ethylacetate, and dried in a vacuum oven at 80° C. to give 7.7 grams of a white powder of 5-(1-(3-nitrophenoxy)ethyl)-1,3,4-thiadiazol-2-yl isocyanate dimer (m. p. 190–200 (decomposes) °C.).

c. Formation of 3-[5-(3-nitrophenoxy)ethyl)-1,3,4-thiadiazol-2-yl]-1-methyl-1-(2,2-dimethoxyethyl) urea The procedure of Example I c. was followed using 7.7 grams of the 5-(1-(3-nitrophenoxy)ethyl)-1,3,4-thiadiazol-2-yl isocyanate dimer (prepared above) and 3.1 grams (0.026 mole) of methylaminoacetaldehyde dimethylacetal, to obtain 11.0 grams of a viscous yellow oil of 3-[5-(3-nitrophenoxy)ethyl)-1,3,4-thiadiazol-2-yl]-1-methyl-1-(2,2-dimethoxyethyl) urea.

d. Formation of 3-[5-(1-(3-nitrophenoxy)ethyl)-1,3,4-thiadiazol-2-yl]-1-methyl-4-hydroxy-2-imidazolidinone The procedure of Example I d. was followed using 4.0 grams of 3-[5-(3-nitrophenoxy)ethyl)-1,3,4-thiadiazol-2-yl]-1-methyl-1-(2,2-dimethoxyethyl) urea (prepared above). The oil which formed upon standing forty (40) hours after refluxing the acidic solution, was extracted with chloroform, and the chloroform phase was dried over anhydrous MgSO$_4$, filtered and topped in a roto-vac at 70° C. to yield 3.7 grams of a yellow oil of 3-[5-(1-(3-nitrophenoxy)ethyl)-1,3,4-thiadiazol-2-yl]-1-methyl-4-hydroxy-2-imidazolidinone.

I.R. (neat): broad OH band at 3350 cm$^{-1}$ and C=O band at 1720 cm$^{-1}$.

NMR (CDCl$_3$): 2.93$\delta$ (singlet-3H), 1.82$\delta$ (doublet-3H), 3.3–4.1$\delta$ (mult., 2H), 5.90$\delta$ (quartet 3H), 6.2$\delta$ (broad mult. 3H), 7.2–7.9$\delta$ (aromatic mult., 4H).

Example III

SYNTHESIS OF 3-[5-[1-(4-nitrophenoxy)ethyl]-1,3,4-thiadiazol-2-yl]-4-hydroxy-1-methyl-2-imidazolidinone a. Formation of 5-[1-(4-nitrophenoxy)ethyl]-2-amino-1,3,4-thiadiazol

The procedure of Example I a. was followed using 2-(4-nitrophenoxy)propionic acid) to form a solid precipitate, which was removed by suction filtration, washed with water, and dried in a vacuum oven at 80° C. to 6.7 grams of pale yellow crystals of 5-[1-(4-nitrophenoxy) ethyl]-2-amino-1,3,4-thiadiazole (m.p. 132°–135° C.).

NMR (DMF-d$_7$): 1.78$\delta$ (doublet, 3H), 5.99$\delta$ (quartet, 1H), 8.22$\delta$ (doublet, 2H), 7.28$\delta$ (doublet, 4H), 7.45$\delta$ (singlet, 4H).

b. Formation of 5-[-1-(4-nitrophenoxy)ethyl]-1,3,4-thiadiazol-2-yl isocyanate dimer The procedure of Example I b. was followed using 6.6 grams of the 5-[1-(4-nitrophenoxy)ethyl]-1-amino-1,3,4-thiadiazole (prepared above). Upon purging with nitrogen overnight, a white solid formed which was slurried with ethylacetate, removed by suction filtration and dried in a vacuum oven at 80° C. to 5.9 grams of a white powder of 5-[-1-(4-nitrophenoxy) ethyl]-1,3,4-thiadiazol-2-yl isocyanate dimer (m.p. 215°–221° C.).

c. Formation of 3-[5-(4-nitrophenoxy)ethyl)-1,3,4-thiadiazol-2-yl]-1-methyl-1-(2,2-dimethyloxyethyl) urea The procedure of Example I c. was followed using 5.9 grams (0.02 mole) of the isocyanate dimer (prepared above) and (0.020 mole) of methylaminoacetaldehyde dimethylacetal to form crystals which were removed by suction filtration, and dried in a vacuum oven at 80° C. to 7.6 grams of white crystals of 3-[5-(4-nitrophenoxy)ethyl)-1,3,4-thiadiazol-2-yl]-1-methyl-1-(2,2-dimethyloxyethyl) urea (m.p. 133°–135° C.).

d. Synthesis of 3-[5-(4-nitrophenoxy)ethyl)-1,3,4-thiadiazol-2-yl]-1-methyl-4-hydroxy-2-imidazolidinone The procedure of Example I d. was followed using 4.1 grams (0.010 mole) of the above prepared urea and 1.5 milliliters of concentrated HCl to form an oil which was extracted with chloroform. The chloroform extract was dried over anhydrous MgSo$_4$, filtered, and topped in a roto-vac at 70° C. to a tacky residue, which was crystalized from the minimum amount of a mixture of chloroform, benzene and diethylether. The crystals were removed by suction filtration and dried in a vacuum oven at 70° C. to 2.3 grams of ivory crystals of 3-[5-(1-(4-nitrophenoxy)ethyl)-1,3,4-thiadiazol-2-yl]-1-methyl-4-hydroxy-2-imidazolidinone (m.p. 160°–165° C.).

INTERMEDIATE COMPOUNDS

Although the other compounds described herein and represented graphically by Formulas III and IV possess no herbicidal properties, and compounds of Formula V possess herbicidal properties, nevertheless, the compounds represented by the Formulas III, IV, and V are very useful because they are intermediates for the synthesis of the novel compounds represented by Formula I.

APPLICATIONS OF THE COMPOSITIONS AGAINST WEEDS

The novel active compounds of Formula I are particularly valuable for weed control because they are toxic to many species and groups of weeds and are relatively nontoxic to many beneficial plants. The exact amount of one or more of the compounds required depends upon a variety of factors, including the hardiness of the particular weed species, the weather, the type of soil, the method of application, the kind of beneficial plants in the same area, and the like. Thus, while the application of up to only about one or two ounces of active compound per acre may be sufficient for good control of a light infestation of weeds growing under adverse conditions, the application of 3 pounds or 10 pounds or more of an active compound of Formula I per acre may be required for good control of a dense infestation of hardy perennial weeds growing under favorable conditions.

a. Examples Of Weeds Which May Be Controlled By the Compounds Described Herein Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds. It is believed that the compositions set forth herein, when applied in a herbicidally effective amount control field pennycress, ryegrass, goosegrass, chickweed, purslane, smartweed, knotweed, wildbuckwheat, kochia, medic, corn cockle, ragweed, sow-thistle, croton, cuphea, dodder, fumitory, groundsel, hempnettle, knawel, spurge, spurry emex, jungle rice, pondweed, dogfennel, carpetweed, bedstraw, ducksalad, naiad, chestgrass, fall panicum, witchgrass, switchgrass, watergrass, teaseed, wild turnip and spangletop; biennials such as wild carrot, matricaria, wild barley, campion, chamomile, burqock, mullein, roundleaved mallow, bull thistle, houndstongue, moth mullein, and purple star thistle; or perennials such as white cockle, perennial ryegrass, quackgrass, canada thistle, hedge bindweed, Bermuda grass, sheep sorrel, curly dock, nutgrass, field chfckweed, dandelion, campanula, field bindweed, Russian knapweed, mesquite, toadflax, yarrow, aster, gromwell, horsetail, ironweed, sesbania, bulrush, cat-tail, wintercress, horsenettle, nutsedge, milkweed, and sicklepod.

(1) Examples of the Important Weeds Which are Controlled by the Novel Compounds The important weeds of the genera against which the novel compounds having the —NO$_2$ (nitro) at the ortho (2) position of the phenoxy radical are the most effective preemergence at 10 pounds per acre are Sida, Datura, Brassica, Digitaria, Sorghum, Sesbania, Ipomoea, Avena and Echinochola. Weeds species against which the compounds of the invention are most effective (preemergence) are: *Sida spinosa* (L) (teaweed), *Datura stromonium* (L) (jimsonweed), *Digitaria sangunalis* (L) (crabgrass), *Brassica kaber* (L) (wild mustard), *Sorghum halepense* (johnsongrass), Sesbania spp. (coffeeweed), *Ipomoea purpurea* (L) Roth (morningglory), *Avena fatua* (wild oats) and *Echinochola crusgalli* (L) (barnyardgrass). When applied preemergence at very low rates, of 5 or more pounds per acre, the weed species most affected by the compounds where R is methyl or ethyl are: Sesbania spp. (coffeeweed), *Sorghum halepense* (L) (johnsongrass), *Ipomea purpurea* (L) Roth (morningglory), *Brassica kaber* (L) (wild mustard) and *Digitaria sanguinalis* (L) (crabgrass).

The important weeds of the genera against which the novel compounds having the —NO$_2$ (nitro) at the meta (3) position of the phenoxy radical are most effective preemergence at 10 pounds per acre are: Sida, Datura, Brassica, Digitaria, Sorghum, Sesbania, Ipomoea, Avena and Echinochola. Weed species against which the compounds of the invention are most effective at 10 pounds per acre (preemergence) are: *Sida spinosa* (L) (teaweed), *Datura stramonium* (L) (jimsonweed), *Brassica kaber* (L) (wild mustard), *Digitaria sangunalis* (L) (crabgrass), *Sorghum halepense* (johnsongrass), Sesbania spp. (coffeeweed), *Avena fatua* (wild oats), *Ipomoea purpurea* (L) Roth (morningglory), and *Echinochola crusgalli* (L) (barnyardgrass). When applied preemergence at very low rates of 5 or more pounds per acre, the weed species most affected by the compounds where R is methyl or ethyl are: Sesbania spp. (coffeeweed) *Datura stramonium* (L) (jimsonweed), *Sida spinosa* (L) (teaweed), *Sorghum halepense* (L) (johnsongrass) and *Digitaria sanguinalis* (L) (crabgrass).

The important weeds of the genera against which the novel compounds having the —NO$_2$ (nitro) at the para (4) position of the phenoxy radical of the invention are most effective preemergence at 10 pounds per acre are: Datura, Cyperus, Setaria, Digitaris, Sorghum, Sesbania, Ipomoea, Avena and Echinochola. Weed species against which the compounds of the invention are most effective (preemergence) are: *Datura stramonium* (L) (jimsonweed), *Cyperus esculentus* (L) (yellow nutsedge), *Sorghum halepense* (johnsongrass), Sesbania spp. (coffeeweed), *Digitaria sanguinalis* (L) (crabgrass), *Setaria glauca* (L) (yellow foxtail), *Ipomoea purpurea* (L) Roth (morningglory), *Avena fatua* (wild oats) and *Echinochola crusgalli* (barnyardgrass). When applied postemergence at rates of 10 or more pounds per acre, the weed species most affected by the compounds where R is methyl or ethyl are: *Datura stramonium* (L) (jimsonweed), *Ipomoea purpurea* (L) Roth (tall morningglory) and *Sorghum halepense* (L) (johnsongrass) and *Brassica kaber* (L) wild mustard.

b. Description of the Method of Controlling Weeds

As used herein and in the Claims, the method of controlling the weeds comprises contacting the weeds with a herbicidally effective amount of a composition represented by the formulas described herein. The term "contacting the weeds" refers to any method of contacting the weeds, both preemergence and postemergence (depending on the compounds or mixtures of the compound described herein), such as applying granules of the compound to the soil prior to emergence, or spraying a solution of the compound or compounds described by the general formula, or any other method known in the art by which the weeds are contacted before they emerge or after they emerge with one or more of the compounds represented by Formulas described herein (particularly Formula I). The phrase "herbicidally effective amount" refers to that amount required under the environmental conditions in order to effectively control, that is, by which the weeds are injured so as not to be able to recover from the application of the compound, or to be killed by the compound.

c. General Application of the Compounds

For practical use of herbicides the compounds of this invention are generally incorporated into herbicidal formulations which comprises an inert carrier and a herbicidally toxic amount of a compound mentioned herein. Such herbicidal formulations enable the active compound to be applied conveniently to the side of the weed infestation in any desired quantity. These formulations can be solids such as dusts, granules, or wettable powders or they can be liquids such as solutions, aerosols, or emulsifiable concentrates.

For example, dusts can be prepared by grinding and blending the active compound with a solid inert carrier such as the talcs, clays, silicas, prophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust composition.

In some cases the active compounds are sufficiently soluble in common organic solvents such as kerosene or xylene so that they can be used directly as solutions in these solvents. Frequently solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal formulation according to this invention is illustrated by the following example, in which the quantities are in parts by weight.

EXAMPLE IV

PREPARATION OF A DUST

| Product of Example I | 10 |
|---|---|
| Powdered Talc | 90 |

The above ingredients are mixed in a mechanical grinder-blender and are ground until a homogeneous, freeflowing dust of the desired particle size is obtained. This dust is suitable for direct application to the site of the weed infestation.

d. Mixtures of Compounds Alone or in Mixtures

Although all of the compounds described herein and represented by the general formula described herein are useful as herbicides, some of these are preferred and are better for applications against weeds. In general, all of the compounds described herein may be used efther alone or together in mixtures. When used in mixtures the amount or ratio of one compound to another may vary from 0.01 to 100.

e. Manner of Application of the Compounds

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulations will comprise from about 0.05 to about 95 percent by weight of the active compounds of this invention. In a preferred embodiment of this invention, the herbicidal formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. Examples of Other Pesticides and Herbicides for Combinations

The other herbicides, defoliants, desiccants, and plant growth inhibitors, with which the compounds of this invention can be used in the herbicidal formulations to control weeds, can include: chlorophenoxy herbicides; such as 2,4-D,2,4,5-T, MCPA, MCPB, 4-(2,4-DB), 2,4-DEB, 4-CPB, 4-CPA, 5-CPP, 2,4,5-TES, 3,4-DA, silvex, and the like; carbamate herbicides such as IPC, CIPC, swep, barban, BCPC, CEPC, CPPC, and the like; thiocarbamate and dithiocarbamate herbicides such as CDEC, metam sodium, EPTC, diallate, PEPC, perbulate, vernolate and the like; substituted urea herbicides such as norea, siduron, dichloroal urea, chloroxuron, cycluron, fenuron, monuron, monuron TCA, diuron, linuron, monolinuron, neburon, buturon, trimeturon, and the like; symmetrical triazine herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alphachloro-N-isopropyl-acetamide, 2-chloro-N-isopropylacetanilide, 4-(chloroacetyl) morpholine, 1-(chloroacetyl) piperidine, and the like; chlorinated aliphatic acid herbicides such as TCA, dalapon, 2,3-dichloropropionic acid, 2,2,3-TPA, and the like; chlorinated benozic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenyl-acetic acid, 2-methoxy-3,5,6-trichlorophenylacetic acid, 2,5-dichloro-3-nitrobenzoic acid, dual, metribuzin and the like; and such compounds as aminotriazole, maleic hydrazode, phenyl mercuric acetate, endothall, biuret, technical chlordane, dimethyl 2,3,5,6-tetrachloratetephthalate, diquat, erbon, DNC, DNBP, dichlorobenil, CPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dine, bromoxynil, cacodylic acid, CMA, CPMF, cypromid, DCB, DCPA, dichlone, diphenatril, DMTT, DNAP, EXD, ioxynil, isocil, potassium cyanate, MAA, MAMA, MCPES, MCPP, MH, molinate, NPA, paraquat, PCP, picloram, DPA, PCA, pyrichlor, sesone, terbacil, terbutol, TCBA, LASSO, planavin, sodium tetraborate, calcium cyanamide, DEF, ethyl xanthogen disulfide, sindone, sindone B, propanil and the like. Such herbicides can also be used with the compositions of this invention in the form of their salts, esters, amides, and other derivatives whenever applicable to the particular parent compounds.

The following examples illustrate the method of controlling the weeds described herein. These examples were conducted under standard laboratory conditions, using standard laboratory procedures for testing compounds preemergence.

Example V

When the compound 3-[5-[1-(2-nitrophenoxy ethyl]-1,3,4-thiadiazol-2-yl]-4-hydroxy-1-methyl-2-imidazolidinone (Example I) was applied preemergence at 10 pounds per acre to the weed species *Sida spinosa* (L) (teaweed), *Datura stramonium* (L) (jimsonweed), *Brassica kaber* (L) (wild mustard), *Digitaria sanguinalis* (L) (crabgrass), *Sorghum halepense* (L) (johnsongrass), Sesbania species (coffeeweed), *Ipomoea purpurea* (L) Roth (morningglory), *Avena fatua* (wild oats) and *Echinochola cursgalli* (L) (barnyardgrass), all of the weed species were either severely injured or killed at the end of 21 days.

EXAMPLE VI

When the compound 3-[5-[1-(3-nitrophenoxy)ethyl]-1,3,4-thiadiazol-2-yl]-4-hydroxy-1-methyl-2-imidazolidinone (Example II) was applied preemergence at 10 pounds per acre to the weed species *Sida spinosa* (L) (teaweed), *Datura stramonium* (L) (jimsonweed), *Brassica kaber* (L) (wild mustard), *Digitaria sanguinalis* (L) (crabgrass), *Sorghum halepense* (L) (johnsongrass), Sesbania species (coffeeweed), *Ipomoea purpurea* (L) Roth (morningglory), *Avena fatua* (wild oats) and *Echinochola cursgalli* (L) (barnyardgrass), all of the weed species were either severely injured or killed at the end of 21 days.

Example VII

When the compound 3-[5-[1-(4-nitrophenoxy)ethyl]-1,3,4-thiadiazol-2-yl]-4-hydroxy-1-methyl-2-imidazolidinone (Example III) was applied premergence at 10 pounds per acre to the weed species *Sida spinosa* (L) (teaweed), *Datura stramonium* (L) (jimsonweed), *Cyperus esculentus* (L) (yellow nutsedge), *Sorghum halepense* (L) (johnsongrass), *Digitaria sanguinalis* (L) (crabgrass), Sesbania species (coffeeweed), *Setaria glauca* (L) yellow foxtail), *Avena fatua* (wild oats) *Ipomoea purpura* (L) Roth (morningglory) and *Echinochola crusgalli* (L) (barnyardgrass), all of the weed species were either severely injured or killed at the end of 21 days.

Example VIII

When the compound 3-[5-[1-(2,4-dichlorophenoxy)-methyl]-1,3,4-thiadiazol-2-yl]-4-hydroxy-1-methyl-2-imidazolidinone (prepared in similar manner to compounds described herein), was applied preemergence at 10 pounds per acre to the weed species *Sida spinosa* (L) (teaweed), *Datura stramonium* (L) (jimsonweed), *Brassica kaber* (L) (wild mustard), *Digitaria sanguinalis* (L) (crabgrass), *Sorghum halepense* (L) (johnsongrass), Sesbania species (coffeeweed), *Ipomoea purpurea* (L) Roth (morningglory), *Avena fatua* (wild oats) and *Echinochola cursgalli* (L) (barnyardgrass), all of the weed species were still growing at the end of 21 days.

Furthermore, some of the compounds, particularly the preferred compounds mentioned herein when applied at very low rates, for example below 1 and 2 pounds per acre will not affect crops such as soybeans and wheats.

While the invention has been described with reference to the specific details of certain illustrative embodiments, it is not intended that it shall be limited thereby except so far as such details appear in the accompanying claims.

I claim:

1. A compound graphically represented by Formula III

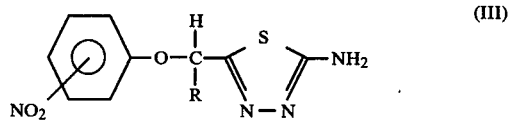

(III)

wherein:

R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 2-bromoethyl.

2. The compound as recited in claim 1 wherein R is an alkyl selected from the group consisting of methyl and ethyl.

* * * * *